United States Patent [19]

Georgiev et al.

[11] Patent Number: 4,831,154

[45] Date of Patent: * May 16, 1989

[54] 5-ALKYL(OR ALKENYL)-3-PHENYL-3-(1H-IMIDAZOL-1-YLMETHYL)-2-METHYLISOXAZOLIDINES

[75] Inventors: Vassil S. Georgiev, Rochester; George B. Mullen, Avon, both of N.Y.

[73] Assignee: Pennwalt Corporation, Philadelphia, Pa.

[ * ] Notice: The portion of the term of this patent subsequent to Sep. 6, 2005 has been disclaimed.

[21] Appl. No.: 36,828

[22] Filed: Apr. 10, 1987

[51] Int. Cl.$^4$ .................. A01N 43/74; C07D 261/02
[52] U.S. Cl. .................. 548/240; 548/341
[58] Field of Search ..................... 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |
| 4,727,156 | 2/1988 | Georgiev | 548/240 |
| 4,727,157 | 2/1988 | Georgiev | 548/240 |
| 4,749,793 | 6/1988 | Georgiev | 548/240 |
| 4,754,042 | 6/1988 | Georgiev | 548/240 |

FOREIGN PATENT DOCUMENTS

171137 2/1986 European Pat. Off. ............ 548/215
54-76579 6/1979 Japan .

OTHER PUBLICATIONS

Sokolov, S. V. et al., Chemical Abstract 55:7399 (1961) Abstracting "Isoxazole Compounds III, Synthesis of some isoxazolylazoles", Zhur. Obshchei Khim. 30 pp. 1781-1787 (1960).
Kano, H. et al., Chem. Abstract 62:9139A (1965) Abstracting French 1,376,432 (Oct. 23, 1964).
Kano, H. et al., Chem. Abstract 63:8367a (1965) Abstracting French 1,380,177 (Nov. 27, 1964).
Takahi, Y. et al., Chem. Abstract 81:22233c (1974) Abstracting Japan Kokai 7399,336 (Dec. 15, 1973).
Boyce, C. B. et al., Chem. Abstract 87:23258a (1977), Abstracting German Offen. 2,639,189 (Mar. 10, 1977).
Funaki, Y. et al., Chem. Abstract 92:128915u (1980), Abstracting Japan Kokai 79, 76,579 (Jun. 19, 1979).
Kelly, R. C. et al., Chem. Abstract 93:114498u (1980), Abstracting German Offen. 2,918,878 (Nov. 22, 1979).
Haken, P. T. et al., Chem. Abstract 93:132471i (1980), Abstracting Brit. Pat. Appln. 2,024,218 (Jan. 9, 1980).

*Primary Examiner*—Anton H. Sutto
*Assistant Examiner*—Mark W. Noel
*Attorney, Agent, or Firm*—Seidel, Gonda, Lavorgna & Monaco

[57] ABSTRACT

5-alkyl(oralkenyl)-3-phenyl-3-(1H-imidazol-1-ylmethyl)-2-methylisoxazolidines and related derivatives in which hydrogens of their phenyl rings can be replaced by halogen, lower alkyl or lower alkoxy groups are useful as antifugal agents.

11 Claims, No Drawings

5-ALKYL(OR ALKENYL)-3-PHENYL-3-(1H-IMIDAZOL-1-YLMETHYL)-2-METHYLISOXAZOLIDINES

BACKGROUND OF THE INVENTION

This invention relates generally to substituted 2-methylisoxazolidines and more specifically to 5-alkyl(or alkenyl)-3-phenyl-(1H-imidazol-1-ylmethyl)-2-methylisoxazolidines and related derivatives which are useful as antifungal agents.

BRIEF SUMMARY OF THE INVENTION

In accordance with this invention these are provided compounds of the formula:

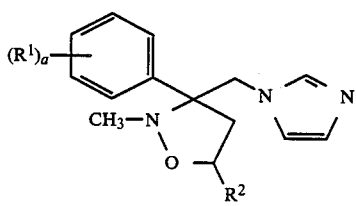

and the pharmaceutically acceptable acid addition salts thereof, in the form of their enantiomers or mixtures of their enantiomers including diastereoisomeric pairs of such enantiomers, wherein;

a=1 or 2, $R^1$ is selected from hydrogen, lower alkyl, lower alkoxy, halogen, and combinations thereof, provided that the ortho position is hydrogen, and $R^2$ is selected from phenylalkyl, substituted phenylalkyl, phenylalkenyl, substituted phenylalkenyl, $C_1$ to $C_{18}$ alkyl, (cycloalkyl)alkyl, and (alkoxycarbonyl)alkyl groups wherein the phenyl substitutents are selected from one or more of lower alkyl, lower alkoxy, and halogen including combinations thereof.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., Laboratory Handbook of Medical Mycology, Academic Press, N.Y., N.Y. (1980)]. The compounds prepared in Examples 1-3 and 9 were found to have good to moderate inhibitory activity against a broad spectrum of organisms including trichophyton mentagrophytes, trichophyton rubrum, trichophyton tonsurans, epidermophyton floccosum and candida stellatoidea. The compound of Example 10 was active against trichophyton rubrum, aspergillis fumigatus and candida albicans (minimum inhibitory concentration, MIC, of <0.2 to 70 ug/ml).

Because of their antifungal activity, the compounds of the invention can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

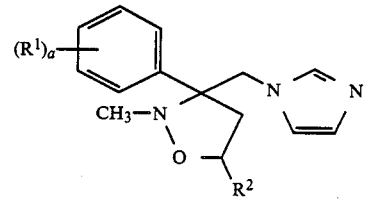

and the pharmaceutically acceptable acid addition salts thereof, in the form of their enantiomers or mixtures of their enantiomers including diastereoisomeric pairs of such enantiomers, wherein;

a=1 or 2, $R^1$ is selected from hydrogen, lower alkyl, lower alkoxy, halogen, and combinations thereof, provided that the ortho position is hydrogen, and $R^2$ is selected from phenylalkyl, substituted phenylalkyl, phenylalkenyl, substituted phenylalkenyl, $C_1$-$C_{18}$ alkyl (branched or unbranched chain), (cycloalkyl)alkyl, and (alkoxycarbonyl)alkyl groups wherein the phenyl rings can be substituted with one or more substituents including lower alkyl, lower alkoxy, halogen and combinations thereof.

By halogen is meant chlorine, bromine, fluorine and iodine with chlorine and fluorine being preferred. By lower alkyl is meant alkyl groups containing one to four (1-4) carbons and by lower alkoxy is meant alkoxy groups containing one to six (1-6) carbons. In either case such groups with three or more carbons can have a branched or unbranched chain. By cycloalkyl (alkyl) is meant a $C_1$ to $C_4$ alkyl group substituted with a $C_3$ to $C_8$ cycloalkyl group and by (alkoxycarbonyl) alkyl is meant a $C_1$ to $C_4$ alkyl group substituted with a $C_1$-$C_6$ alkoxy carbonyl group. Compounds having ortho substitution of the 3-phenyl group were not prepared probably due to steric hindrance.

The 5-alkyl(or alkenyl)-3-phenyl-3-(1H-imidazol-1-yl-methyl)-2-methylisoxazolidine derivatives of the invention are obtained as a mixture of cis- and trans-diastereomers due to the presence of two asymmetric carbon atoms in the isoxazolidine ring. The diastereomeric mixture is conveniently separated by flash-chromatography on silica gel using halogenated hydrocarbons (preferably dichloromethane and chloroform), alkanols (preferably methanol and ethanol), ethyl acetate and such, as eluents. The eluents may be used alone or in combinations such as the ones comprised of 95-99% halogenated hydrocarbon and 1-5% alkanol by volume. The stereochemistry of the two asymmetric carbons atoms in the isoxazolidine ring may be determined by conventional methods that include x-ray crystallography, nuclear magnetic resonance spectroscopy, circular dichroism and optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−)-tartaric acid, (+) and (−)-dibenzoyltartaric acid and the like.

The compounds of the invention can be prepared as illustrated in the following diagram. The synthesis of the nitrone precursors 1 is accomplished by reacting an appropriately substituted 2-imidazolylacetophenone with N-methylhydroxylamine as described in our co-pending application serial number 900,856 filed Aug. 27, 1986 whose disclosure is incorporated herein by reference. Subsequent reaction of the nitrone with an appropriate 1-alkene derivative 2 having 3 to 21 carbons in the carbon chain provides a diastereomeric mixture of the desired cis- and trans-5-alkyl(or alkenyl)-3-phenyl-3-(1H-imidazol-1-yl-methyl)-2-methylisoxazolidine derivative 3.

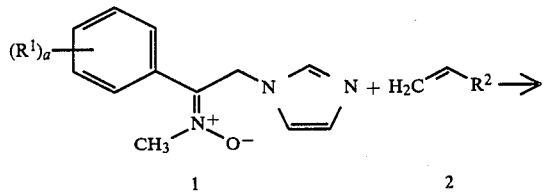

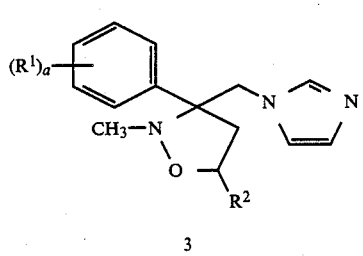

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following examples.

EXAMPLE 1

5-(Phenylmethyl)-3-(4-chlorophenyl)-3-(1H-imidazol-1-ylmethyl)-2-methylisoxazolidine (3: $R^1$=4-Cl, $R^2$=CH$_2$C$_6$H$_5$)

A solution of 7.04 g (0.0282 mol) of 1-(4-chlorophenyl)-2-(1H-imidazol-1-yl)-N-methylethanimine N-oxide (1: $R^1$=4-Cl) [prepared by reacting 2-(1H-imidazol-1-yl)-4'-chloroacetophenone (45.05 g, 0.204 mol), N-methylhydroxylamine hydrochloride (20.93 g, 0.251 mol), and sodium acetate (41.13 g, 0.502 mol) in 550 ml of ethanol] and 3.95 g (0.0334 mol) of allylbenzene (2: $R^2$=CH$_2$C$_6$H$_5$) in 100 ml toluene is refluxed for 30 hours under a nitrogen atmosphere. Upon cooling to room temperature, the solvent is removed in vacuo. The resulting cis-/trans-diastereomeric mixture of compound 3 ($R^1$=4-Cl, $R^2$=CH$_2$C$_6$H$_5$ is flash-chromatographed on neutral silica gel using a 98:2 by volume mixture of chloroform and methanol as eluent to give 3.80 g (36%) of isomer A. Following crystallization from ether a melting point of 118°–120° C. is determined.

Anal. Calcd. for C$_{21}$H$_{22}$ClN$_3$O: C, 68.56; H, 6.03, N, 11.42. Found: C, 68.66; H, 6.16; N, 11.51.

EXAMPLE 2

5-n-Hexyl-3-(4-chlorophenyl)-3-(1H-imidazol-1-ylmethyl)-2-methylisoxazolidine (3: $R^1$=4-Cl, $R^2$=(CH$_2$)$_5$CH$_3$)

Compound 3 ($R^1$=4-Cl, $R^2$=(CH$_2$)$_5$CH$_3$) is prepared by a method similar to that described in Example 1 by reacting 1-(4-chlorophenyl)-2-(1H-imidazol-1-yl)-N-methylethanimine N-oxide (1: $R^1$=4-Cl) with 1-octene [2: $R^2$=(CH$_2$)$_5$CH$_3$]. The resulting cis-/trans-diastereomeric mixture of compound 3 ($R^1$=4-Cl, $R^2$=(CH$_2$)$_5$CH$_3$) is flash-chromatographed on neutral silica gel using ethyl acetate as eluent. Isomer A has a melting point of 129°–132° C. (ethyl acetate) as its hydrochloride salt.

Anal. Calcd. for C$_{20}$H$_{29}$Cl$_2$N$_3$O: C, 60.30; H, 7.34; N, 10.55; Cl, 17.80. Found: C, 60.27; H, 7.28; N, 10.50; Cl, 17.29.

EXAMPLE 3

5-n-Decyl-3-(4-chlorophenyl)-3-(1H-imidazol-1-ylmethyl)-2-methylisoxazolidine (3: $R^1$=4-Cl, $R^2$=(CH$_2$)$_9$CH$_3$)

Compound 3 ($R^1$=4-Cl, $R^2$=(CH$_2$)$_9$CH$_3$) is prepared by a method similar to that described in Example 1 by reacting 1-(4-chlorophenyl)-2-(1H-imidazol-1-yl)-N-methylethanimine N-oxide (1: $R^1$=4-Cl) with 1-dodecene (2: $R^2$=(CH$_2$)$_9$CH$_3$). The resulting cis-/trans-diasteromeric mixture of compound 3 ($R^1$=4Cl, $R^2$=(CH$_2$)$_9$CH$_3$) is flash-chromatographed on neutral silica gel using ethyl acetate as eluent. Isomer A has a melting point of 75°–80° C. (acetonitrile).

Anal. Calcd. for C$_{24}$H$_{36}$ClN$_3$O: C, 68.96; H, 8.68; N, 10.05; Cl, 8.48. Found: C, 68.96; H, 8.65; N, 10.11; Cl, 8.64.

EXAMPLE 4

5-n-Tetradecyl-3-(4-chlorophenyl)-4-(1-H-imidazol-1-ylmethyl)-2-methylisoxazolidine (3: $R^1$=4-Cl, $R^2$=(CH$_2$)$_{13}$CH$_3$)

Compound 3 ($R^1$=4-Cl, $R^2$=(CH$_2$)$_{13}$CH$_3$) is prepared by a method similar to that described in Example 1 by reacting 1-(4-chlorophenyl)-2-(1H-imidazol-1-yl)-N-methylethanimine N-oxide (1: $R^14$-Cl) with 1-hexadecene (2: $R^2$=(CH$_2$)$_{13}$CH$_3$). The resulting cis-/trans-diastereomeric mixture of compound 3 ($R^1$=4-Cl, $R^2$=(CH$_2$)$_{13}$CH$_3$) is flash-chromatographed on neutral silica gel using ethyl acetate as eluent. Isomer A has a melting point of 82°–86° C. (ethyl acetate).

Anal. Calcd. for C$_{28}$H$_{44}$ClN$_3$O: C, 70.93; H, 9.35; N, 8.86; Cl, 7.48. Found: C, 70.95; H, 9.43; N, 8.87; Cl, 7.76.

EXAMPLE 5

5-n-Hexadecyl-3-(4-chlorophenyl)-4-(1H-imidazol-1-ylmethyl)-2-methylisoxazolidine (3: $R^1$=4-Cl, $R^2$ (CH$_2$)$_{15}$CH$_3$)

Compound 3 ($R^1$=4-Cl, $R^2$=(CH$_2$)$_{15}$CH$_3$) is prepared by a method similar to that described in Example 1 by reacting 1-(4-chlorophenyl)-2-(1H-imidazol-1-yl)-N-methylethanimine N-oxide (1, $R^1$=4-Cl) with 1-octadecene (2: $R^2$=(CH$_2$)$_{15}$CH$_3$). The resulting cis-/trans-diastereomeric mixture of compound 3 ($R^1$=4-Cl, $R^2$=(CH$_2$)$_{15}$CH$_3$) is flash-chromatographed on neutral silica gel using ethyl acetate as eluent. Isomer A has a melting point of 86°–90° C. (ethyl acetate).

Anal. Calcd. for C$_{30}$H$_{48}$ClN$_3$O: C, 71.75; H, 9.63; N, 8.37; Cl, 7.06. Found: C, 71.77; H, 9.62; N, 8.35; Cl, 7.15.

EXAMPLE 6

5-n-Octadecyl-3-(4-chlorophenyl)-3-(1H-imidazol-1-ylmethyl)-2-methylisoxazolidine (3: $R^1$=4-Cl, $R^2$=(CH$_2$)$_{17}$CH$_3$)

Compound 3 ($R^1$=4-Cl, $R^2$=(CH$_2$)$_{17}$CH$_3$) is prepared by a method similar to that described in Example 1 by reacting 1-(4-chlorophenyl)-2-(1H-imidazol-1-yl)-N-methylethanimine N-oxide (1, $R^1$=4-Cl) with 1-eicosene (2: $R^2$=(CH$_2$)$_{17}$CH$_3$). The resulting cis-/trans-diastereomeric mixture of compound 3 ($R^1$=4-Cl, $R_2$=(CH$_2$)$_{17}$CH$_3$) is flash-chromatographed on neutral silica gel using a 98:2 by volume mixture of chloroform and methanol as eluent. Isomer A has a melting point of 81°–86° C. (ether).

Anal. Calcd. for C$_{32}$H$_{52}$ClN$_3$O: C, 72.49; H, 9.89; N, 7.92; Cl, 6.69. Found: C, 72.57; H, 9.85; N, 7.87; Cl, 6.81.

EXAMPLE 7

5-(Cyclopentylmethyl)-3-(4-fluorophenyl)-3-(1H-imidazol-1-ylmethyl)-2-methylisoxazolidine (3, $R^1$=4-F, $R^2$=CH$_2$C$_2$H$_9$(c))

Compound 3 ($R^1$=4-F, $R^2$=CH$_2$C$_5$H$_9$(c)) is prepared by a method similar to that described in Example 1 by reacting 1-(4-fluorophenyl)-2-(1H-imidazol-1-yl)-N-methylethanimine N-oxide (1: $R^1$=4-F) with allylcyclopentane (2: $R^2$=CH$_2$C$_5$H$_9$(c)). The resulting cis-/trans-diastereomeric mixture of compound 3 ($R^1$=4-F, $R^2$=CH$_2$C$_5$H$_9$(c)) is flash-chromatographed on neutral silica gel using a 98:2 by volume mixture of chloroform and methanol as eluent. Isomer A has a melting point of 111°–114° C. (ethyl acetate).

Anal. Calcd. for C$_{20}$H$_{26}$FN$_3$O: C, 69.94; H, 7.63; N, 12.23; F, 5.53. Found: C, 70.15; H, 7.54; N, 12.20; F, 5.19.

EXAMPLE 8

5[2,2-Bis(ethoxycarbonyl)ethyl]-3-(4-fluorophenyl)-3-(1H-imidazol-1-ylmethyl)-2-methylisoxazolidine (3, $R^1$=4-F, $R^2$=CH$_2$CH(CO$_2$Et)$_2$)

Compound 3 ($R^1$=4-F, $R^2$=CH$_2$CH(CO$_2$Et)$_2$) is prepared by a method similar to that described in Example 1 by reacting 1-(4-fluorophenyl)-2-(1H-imidazol-1-yl)-N-methylethanimine N-oxide (1: $R^1$=4-F) with diethyl allylmalonate (2: $R^2$=CH$_2$CH(CO$_2$Et)$_2$). The resulting cis-/trans-diastereomeric mixture of compound 3 ($R^1$=4-F, $R^2$=CH$_2$CH(CO$_2$Et)$_2$) is flash-chromatographed on neutral silica gel using a 99:1 by volume mixture of chloroform and methanol as eluent. Isomer A has a melting point of 75°–78° C. (ether). Isomer B has a melting point of 68°–71° C. (ether)., Anal. Calcd. for C$_{22}$H$_{28}$FN$_3$O$_5$: C, 60.96; H, 6.51; N, 9.69; F, 4.38. Found: C, 61.09; H, 6.58; N, 9.57; F, 4.29.

EXAMPLE 9

5-(2-trans-Phenylethenyl)-3-(4-chlorophenyl)-3-(1H-imidazol-1-ylmethyl)-2-methylisoxazolidine (3: $R^1$=4-Cl, $R^2$=CH=CHC$_6$H$_5$(t)

Compound 3 ($R^1$=4-Cl, $R^2$=CH=CHC$_6$H$_5$(t)) is prepared by a method similar to that described in Example 1 by reacting 1-(4-chlorophenyl)-2-(1H-imidazol-1-yl)-N-methylethanimine N-oxide (1: $R^1$=4-Cl) with trans-1-phenyl-1,3-butadiene (2: $R^2$=CH=CHC$_6$H$_5$(t)). The resulting cis-/trans-diastereomeric mixture of compound 3 ($R^1$=4-Cl, $R^2$=CH=CHC$_6$H$_5$(t)) is flash-chromatographed on neutral silica gel using a 98:2 by volume mixture of chloroform and methanol as eluent. Isomer A has a melting point of 101°–104° C. (ethyl acetate-hexane, 1:1 by volume).

Anal. Calcd. for C$_{22}$H$_{22}$ClN$_3$O: C, 69.56; H, 5.84; N, 11.06; Cl, 9.33. Found: C, 69.36; H, 5.90; N, 11.02; Cl, 9.36.

EXAMPLE 10

5-(2-trans-Phenylethenyl)-3-(4-fluorophenyl)-3-(1H-imidazol-1-ylmethyl)-2-methylisoxazolidine (3: $R^1$=4-F, $R^2$=CH=CHC$_6$H$_5$(t))

Compound 3 ($R^1$=4-F, $R^2$=CH=CHC$_6$H$_5$(t)) is prepared by a method similar to that described in Example 1 by reacting 1-(4-fluorophenyl)-2-(1H-imidazol-1-yl)-N-methylethanimine N-oxide (1: $R^1$=4-F) with trans-1-phenyl-1,3-butadiene (2: $R^2$=CH=CHC$_6$H$_5$(t)). The resulting cis-/trans-diastereomeric mixture of compound 3 ($R^1$=4-F, $R^2$=CH=CHC$_6$H$_5$(t)) is flash-chromatographed on neutral silica gel using a 98:2 by volume mixture of chloroform and methanol as eluent. Isomer A has a melting point of 142°–144° C. (ethyl acetate-hexane, 1:1 by volume).

Anal. Calcd. for C$_{22}$H$_{22}$FN$_3$O: C, 72.71; H, 6.10; N, 11.56; F, 5.23. Found: C, 72.90; H, 6.07; N, 11.56; F, 5.16.

Other compounds of the invention where $R^1$ represents hydrogen or mono or disubstitution with halogen, lower alkyl and/or lower alkoxy are prepared starting with nitrones 1 form from imidazolylacetophenones such as:

2-(1H-imidazol-1-yl)-4'-methylacetophenone, mp 133°–137° C., 2-(1H-imidazol-1-yl)-4'-methoxyacetophenone, mp 134°–137° C.

2-(1H-imidazol-1-yl)acetophenone, mp 117°–119° C., 2-(1H-imidazol-1-yl)-3',4'-dichloroacetophenone, mp 124°–126° C., 2-(1H-imidazol-1-yl)-4'-chloro-3'-methylacetophenone, mp 116°–118° C., 2-(1H-imidazol-1-yl)-3'-methoxyacetophenone, mp 111°–113° C., and 2-(1H-imidazol-1-yl)-3'-methylacetophenone.

The compounds of the invention where $R^2$ includes substituted phenylalkyl can be prepared according to the method of Example 1 by substituting for allylbenzene the following 3-(substituted phenyl)-1-propenes, 3-(4-methylphenyl)-1-propene, bp. 183°–186° C., 3-(4-methoxyphenyl)-1-propene, bp. 216° C., and 3-(4-chlorophenyl)-1-propene, bp. 52° C./0.8 mm The compounds of the invention where $R^2$ includes substituted phenylalkenyl can be prepared according the method of Example 9 by substituting for trans-1-phenyl-1-3-butadiene the following 1-(substituted phenyl)-1,3-butadienes, trans-1-(4-methylphenyl)-1,3-butadiene, mp 26° C., trans-1-(4-methoxyphenyl)-1,3-butadiene, mp 46° C., trans-1-(4-chlorophenyl)-1,3-butadiene, mp 18° C.

Salts of the compounds of the invention can be prepared as known in the art, for example, by dissolving the compound in a 10:1 by volume mixture of ethanol and aqueous acid such as HCl or HNO$_3$, evaporating the solvent, and then recrystallizing the crude salt, for example, from methanol-ether, 1:3 by volume, in the case of HCl salts, and ethanol in the case of HNO$_3$ salts.

We claim:

1. A compound of the formula:

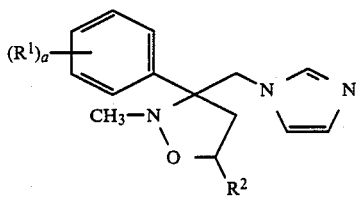

and the pharmaceutically acceptable acid addition salts thereof, in the form of their enantiomers or mixtures of their enantiomers including diastereoisomeric pairs of such enantiomers, wherein;

a = 1 or 2, $R^1$ is selected from hydrogen, lower alkyl, lower alkoxy, halogen, and combinations thereof, provided that the ortho position is hydrogen, and $R^2$ is selected from phenyl ($C_1$ to $C_4$ alkyl), substituted phenyl ($C_1$ to $C_4$ alkyl), phenyl ($C_2$ alkenyl), substituted phenyl ($C_2$ alkenyl), $C_1$ to $C_{18}$ alkyl, ($C_3$ to $C_8$ cycloalkyl) ($C_1$ to $C_4$ alkyl), and ($C_1$ to $C_6$ alkoxycarbonyl) ($C_1$ to $C_4$ alkyl) groups wherein the substituents on phenyl are selected from 1 to 3 of lower alkyl, lower alkoxy and halogens including combinations thereof.

2. The compound of claim 1 wherein the compound is 5-(phenylmethyl)-3-(4-chlorophenyl)-3-(1H-imidazol-1-yl-methyl)-2-methylisoxazolidine.

3. The compound of claim 1 wherein the compound is 5-n-hexyl-3-(4-chlorophenyl)-3-(1H-imidazol-1-ylmethyl)-2-methylisoxazolidine.

4. The compound of claim 1 wherein the compound is 5-n-decyl-3-(4-chlorophenyl)-3-(1H-imidazol-1-ylmethyl)-2-methylisoxazolidine.

5. The compound of claim 1 wherein the compound is 5-n-tetradecyl-3-(4-chlorophenyl)-3-(1H-imidazol-1-ylmethyl)-2-methylisoxazolidine.

6. The compound of claim 1 wherein the compound is 5-n-hexadecyl-3-(4-chlorophenyl)-3-(1H-imidazol-1-ylmethyl)-2-methylisoxazolidine.

7. The compound of claim 1 wherein the compound is 5-n-octadecyl-3-(4-chlorophenyl)-3-(1H-imidazol-1-ylmethyl)-2-methylisoxazolidine.

8. The compound of claim 1 wherein the compound is 5-(cyclopentylmethyl)-3-(4-fluorophenyl)-3-(1H-imidazol-1-ylmethyl)-2-methylisoxazolidine.

9. The compound of claim 1 wherein the compound is 5-[2,2-bis(ethoxycarbonyl)ethyl]-3-(4-fluorophenyl)-3-(1H-imidazol-1-ylmethyl)-2-methylisoxazolidine.

10. The compound of claim 1 wherein the compound is 5-(2-trans-phenylethenyl)-3-(4-chlorophenyl)-3-(1H-imidazol-1-ylmethyl)-2-methylisoxazolidine.

11. The compound of claim 1 wherein the compound is 5-(2-trans-phenylethenyl)-3-(4-fluorophenyl)-3-(1H-imidazol-1-ylmethyl)-2-methylisoxazolidine.

* * * * *